United States Patent [19]

Cote

[11] 4,230,103
[45] Oct. 28, 1980

[54] ORTHOPEDIC DEVICE

[76] Inventor: Renald A. Cote, 1021 26th St., NW., Washington, D.C. 20037

[21] Appl. No.: 966,192

[22] Filed: Nov. 30, 1978

[51] Int. Cl.³ ............................................. A61F 3/00
[52] U.S. Cl. ........................ 128/80 A; 128/DIG. 15
[58] Field of Search ...................... 128/80, 581–585, 128/87, DIG. 15

[56] References Cited

U.S. PATENT DOCUMENTS

| | | | |
|---|---|---|---|
| 2,482,646 | 9/1949 | Brachman et al. | 128/80 A |
| 2,514,870 | 7/1950 | Israel | 128/80 A |
| 2,920,620 | 1/1960 | Rogers | 128/583 |
| 3,477,426 | 11/1969 | Wincheski | 128/80 R |
| 3,523,526 | 8/1970 | Phelps | 128/80 R |
| 3,762,421 | 10/1973 | Sax, Sr. | 128/583 |
| 3,834,377 | 9/1974 | Lebold | 128/DIG. 15 |
| 3,892,231 | 7/1975 | Tummillo | 128/87 C |
| 3,910,267 | 10/1975 | Reiman | 128/80 A |
| 3,931,817 | 1/1976 | Infranca | 128/80 A |
| 3,973,559 | 8/1976 | Reiman | 128/80 A |
| 4,019,504 | 4/1977 | Sterling | 128/DIG. 15 |

FOREIGN PATENT DOCUMENTS 1456621  2/1973  U.S.S.R. ........................... 128/80 J

*Primary Examiner*—Robert W. Michell
*Assistant Examiner*—Thomas J. Wallen
*Attorney, Agent, or Firm*—Cushman, Darby & Cushman

[57] ABSTRACT

An orthopedic assembly for the treatment of congenital and acquired deformities in children's legs or feet that provide for continuous adjustment of the child's shoes to the assembly, and are readily removable. The assembly comprises a pair of plate members each substantially larger than a child's shoe, a bar for attaching the plate members together and VELCRO fasteners between the bottoms of the child's shoes and the plate members. A tab is provided on each of the shoe bottoms to facilitate release of the fasteners on the shoe bottoms and plate members. Indicia preferably are provided on the plate members to indicate relative orientations that the shoes may assume with respect to the plate members.

7 Claims, 4 Drawing Figures

ORTHOPEDIC DEVICE

BACKGROUND AND SUMMARY OF THE INVENTION

The present invention relates to orthopedic devices particularly for use in the treatment of congenital and acquired deformities in children's legs or feet, such as club feet, bow legs, knock knees, foot adductions, and foot abduction. Such abnormal foot and leg conditions may be corrected by rotation of the deformed limbs about one or more axis and then maintaining the limb in that position. Of course, the relative position that the feet should assume to provide corrective action varies significantly from individual to individual, and in fact varies significantly over the treatment time for a particular individual.

While conventional orthopedic devices for correcting such deformities are successful in achieving their desired results, there are normally a number of disadvantages associated therewith. The structure necessary to allow positioning of the child's feet in exactly the proper position for treatment often is complicated to construct, relatively expensive, and very time consuming to adjust. Yet, the positions that the shoes may assume to provide their corrective action are not continuously adjustable, but only incrementally adjustable. Further, the shoes are rigidly attached to the corrective device, and in an emergency situation, detachment is not practical.

According to the present invention, an orthopedic assembly is provided that achieves the corrective action provided by prior art devices at least as effectively as is provided by such prior art devices, provides continuous adjustability of the shoe position to accomodate different individuals and different stages of an individual's treatment and are readily removable and positionable so that no time is wasted in properly positioning the shoes, and provides for ready removal of the shoes in an emergency situation.

The orthopedic assembly according to the present invention comprises a pair of plate members, each substantially larger than a child's shoe; means for operatively attaching the plate members together so that they are disposed in a common plane; and means for operatively attaching the pair of plate members to a pair of child's shoes so that the angular position the shoes may assume relative to the plate members is continuously adjustable, and so that the shoes are readily removable from the plate members. The operatively attaching means preferably comprises cooperating hook and loop fastening means attached to the plate members on faces of each disposed in the same plane, and to the bottom of the shoes. Exemplary cooperating hook and loop fastening means that are utilizable according to the present invention are commercially available VELCRO fasteners, and the term "cooperating hook and loop fastening means" as used in the present specification and claims is intended to encompass VELCRO fasteners and like fastening devices.

Normally, the hook and loop fastening means comprise a piece of fastening means material of substantially the same size as the bottom of a child's shoe associated with each shoe, with adhesive attaching the material to the shoe bottom. Tab means extend past the bottoms of the shoe as an extension of the material, to facilitate release of the cooperating hook and loop fastening means. Indicia are desirably provided on the plate members corresponding to the outline of a child's shoe so that the proper position of the shoe on the plate members can be readily determined during quick and easy fastening thereof. Additionally, the means for operatively attaching the plate members together preferably affix the plate members so that they maintain the same angular orientation with respect to each other so that no complicated rotation allowing means need be provided, and the plate members are linearally adjustable with respect to each other.

It is the primary object of the present invention to provide an orthopedic assembly for the treatment of congenital and acquired deformities in children's legs or feet that is continuously adjustable and readily removable from the child's shoes. This and other objects of the invention will become clear from an inspection of the detailed description of the invention, and from the appended claims.

DETAILED DESCRIPTION OF THE INVENTION

Figure 1:
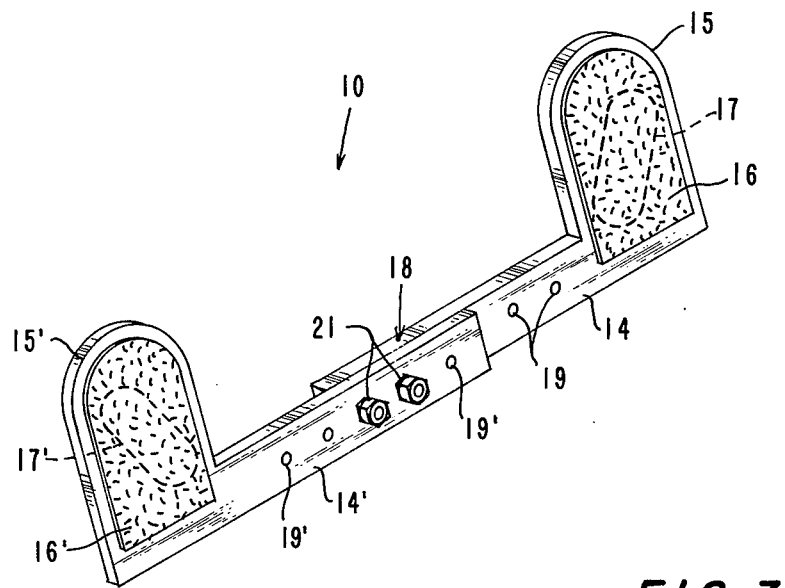
FIG. 1 is a perspective view of exemplary plate numbers according to the present invention, attached together.
Figure 2:
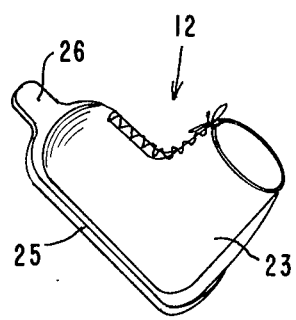
FIG. 2 is a perspective view of an exemplary shoe utilizable with the plate members of FIG. 1.

An exemplary orthopedic assembly according to the present invention is shown at 10 in FIG. 1, and at 12 in FIG. 2. The assembly includes a pair of plate members 15, 15', each substantially larger than a child's shoe (12), with means (bars 14, 14') for operatively attaching the plate members 15, 15' together so that they are disposed in a common plane. The assembly further comprises means for operatively attaching the pair of plate members 15, 15' to a pair of child's shoes (12) so that the angular position the shoes may assume relative to the plate members is continuously adjustable (as opposed to incrementally adjustable), and so that the shoes are readily removable from the plate members. Such attaching means 16, 16' are attached to the plate members 15, 15' on faces of each disposed in the same plane, and to the bottoms of the shoes 12 (see structure 25 in FIG. 3 in particular). Such cooperating hook and loop fastening means preferably comprise VELCRO fasteners, the fastening component 16, 6'being matched with the fasteners on the component 25 so that readily removable attachment between the shoes 12 and plate members 15, 15' is provided.

Because of the cooperating hook and loop fastening means provided on the plates 15, 15' and the shoes 12, the shoes 12 may assume any angular orientation with respect to the plates 15, 15' that is desired, depending on the individual and the particular stage of treatment of the individual. In order to insure that the shoes are properly positioned with respect to the plates at a particular stage of treatment of an individual, it is desirable to provide indicia means 17, 17' on the fastening means 16, 16' associated with the plates 15, 15'. Such indicia means 17, 17' form the outline of the shoe 12, and to operatively position the shoes 12 with respect to the plates 15, 15', it is necessary only to match up the shoe bottoms with the indicia means 17, 17'. A plurality of indicia 17, 17' may be provided on each plate 15, 15', in different colors if desired, and the indicia 17, 17' may be placed on the fastening means 16, 16' by the physician when originally positioning the child's shoes 12 and plates 15, 15' allowing the exact desirable positioning of the shoes.

The bars 14, 14' for operatively attaching the plates 15, 15' together preferably are simple rigid structures that maintain the same angular orientation with respect to the plates 15, 15', and maintain the same relative angular orientation between the plate members 15, 15' at all times. There is no reason to provide complicated pivotal attachment structures between the plate members 15, 15', and the bars 14, 14' since the mere positioning of the shoes 12 on the fastening means 16, 16' takes care of all angular orientations that are necessary. However, it is desirable to effect linear adjustment between the plates 15, 15' to accomodate children of different sizes and having different deformities. Adjustment means 18 preferably are provided to accomplish this. The adjustment means 18 may take any conventional form, such as the form indicated in FIG. 1 wherein holes 19, 19' are provided in the bars 14, 14' for receipt of one or more fasteners 21 locking the bars in the relative position to which they have been moved.

Figure 3:
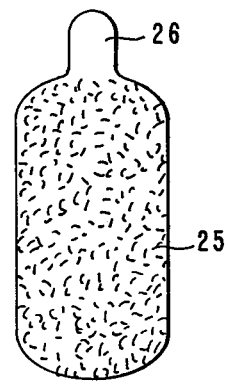
FIG. 3 is bottom plan view of the shoe of FIG. 2.
Figure 4:
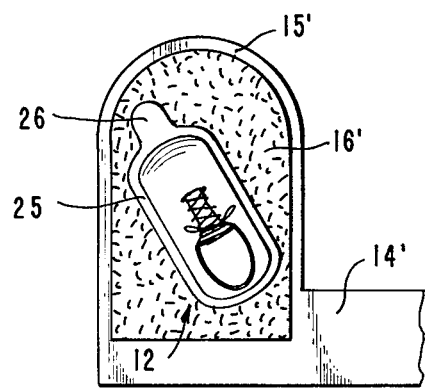
FIG. 4 is a top plan view showing one of the plate members of FIG. 1 with the shoe of FIG. 2 in operative position thereon.

The attachment provided between the fastening means 16, 16' and 25 is extremely secure when vertical or horizontal relative movement between the fastening means 16, 16' and 25 is attempted. However, ready release of the connection between the fastening means 16, 16' and 25 may be effected by a relative "tearing" movement therebetween. In order to facilitate effecting this tearing movement when desirable, tab means 26 are provided associated with the shoes 12. Normally, the fastening means 25 will be provided as a piece of fastening means material (as seen in FIGS. 2-4) of substantially the same size as the bottom of the shoe 12 associated with the shoe, the tab means 26 merely being an extension of that material extending past the bottoms of the shoes 12 and adapted to be grasped by a person's fingers. The fastening means material (25) can be attached to the bottoms of the shoes 12 by any desirable means, such as adhesive. In fact, the attachment between the fastening means material (25) and the shoes bottoms can be readily releaseable so that the shoes 12 can be used for other than orthopedic purposes. The fastening means 16, 16' also may be attached to the plates 15, 15' by any suitable means, such as adhesive, snaps, screws, or the like.

Exemplary apparatus according to the present invention now having been described, an exemplary method of utilization thereof will now be set forth.

A physician having examined a patient and decided on a course of treatment, determines the relative amount of longitudinal rotation of each foot about the normal axis desirable for effecting correction of the patient's deformity, and adjusts the position between the plates 15, 15' by detachment of the fasteners 21 and respositioning them in the desired openings 19, 19' of the bars 14, 14'0 and securing them in place. The child's feet are then inserted in the shoe bodies 23, and each shoe assembly 12 is positioned with respect to the plate members 15, 15' by pushing the VELCRO fasteners 25 associated with the shoe assemblies onto the VELCRO fastening means 16, 16' associated with the plates 15, 15'. Once the proper angular orientation between the shoe assembly and plate members has been achieved, indicia means 17, 17' corresponding to those positions may then be drawn on the VELCRO fastening mean 16, 16' by the physician.

In use, every night, or other times when the relative corrective action provided by the assembly according to the present invention is desired, the child's feet in the shoe bodies 23 are pressed down so that positive engagement is provided between the material 25, and the material 16, 16', the shoe assemblies 12 having been matched up with the indicia 17, 17'. When it is desirable to remove the shoe assemblies 12 from the plate members 15, 15', the tab means 26 are merely grasped by the index and forefinger, and an upward tearing force is applied, readily detaching the fastening means 25 from the fastening means 16, 16'. Ready detachment also is provided for emergency situations.

As the child grows, and as the corrective action must be adjusted, new indicia 17, 17' are provided on the fastening means 16, 16'—or a new piece of fastening means material is provided —the shoe assembly 12 being continuously adjustable with respect to the plate members 15, 15' so that the exact relative orientation between the shoe assemblies 12 and plate members 15, 15' is provided. Since the connection between the bars 14, 14' and the plate members 15, 15' is merely a simple rigid connection, with no relative rotation between the bars 14, 14' and the plates 15, 15' being necessary, the entire assembly 10, 12 is simple and easy and inexpensive to construct, adjust, fit, and utilize.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and devices.

What is claimed is:

1. An orthopedic assembly for attachment to a child's shoes comprising:
   a pair of plate members, each substantially larger than a child's shoe;
   a pair of children's shoes adapted to be operatively attached to said plate members;
   means for operatively attaching said plate members together so that they are disposed in a common plane and so that they cannot rotate with respect to each other or said attaching means; and
   means for operatively attaching said pair of plate members to said pair of child's shoes so that the angular position the shoes may assume relative to the plate members is continuously adjustable, and so that the shoes are readily removable from the plate members, said means comprising cooperating hook and loop fastening means attached to coplanar faces of said plate members, and to the bottoms of said shoes.

2. An assembly as recited in claim 1 further comprising indicia means formed on each said plate members corresponding to the outline of a child's shoe.

3. An assembly as recited as in claim 1 wherein said means for operatively attaching said plate members together allow adjustment of the linear spacing thereof with respect to each other.

4. An orthopedic assembly for attachment to a child's shoes comprising:
   a pair of plate members each substantially larger than a child's shoe;

means for operatively attaching said plate members together so that they are disposed in a common plane;

a pair of children's shoes; and means for operatively attaching said pair of plate members to a pair of children's shoes, said means comprising cooperating hook and loop fastening means attached to coplanar faces of said plate members, and to the bottoms of said children's shoes.

5. An assembly as recited in claim 4 wherein said means for operatively attaching said plate members together affix said plate members so that they maintain the same angular orientation with respect to each other at all times, and are linearly adjustable with respect to each other.

6. An assembly as recited in claims 1 or 4 comprising tab means extending past the bottoms of said shoes and adapted to be grasped to facilitate release of said cooperating hook and loop fastening means.

7. An assembly as recited in claim 6 wherein said hook and loop fastening means comprise a piece of fastening means material of substantially the same size associated with each shoe, and adhesive for attaching said material to shoe bottom, said tab means being an extension of said material.

* * * * *